United States Patent [19]
Marks

[11] Patent Number: 5,314,410
[45] Date of Patent: May 24, 1994

[54] ENTRY INDICATOR DEVICE FOR ARTERIAL OR INTRAVENOUS NEEDLE

[76] Inventor: Ronald L. Marks, 1124 Townsley, Bakersfield, Calif. 93304

[21] Appl. No.: 991,705

[22] Filed: Dec. 16, 1992

Related U.S. Application Data

[63] Continuation-in-part of Ser. No. 832,956, Feb. 10, 1992, abandoned.

[51] Int. Cl.$^5$ ............................................. A61M 5/178
[52] U.S. Cl. ..................................... 604/168; 604/900; A61M/5/178
[58] Field of Search .............................. 604/167–169, 604/900; 128/764

[56] References Cited

U.S. PATENT DOCUMENTS

| | | | |
|---|---|---|---|
| 2,735,428 | 2/1956 | Huber | 604/900 X |
| 2,735,429 | 2/1956 | Huber | 604/900 X |
| 3,089,489 | 5/1963 | Dunmire | 604/900 X |
| 4,108,175 | 8/1978 | Orton | 604/168 |
| 4,487,605 | 12/1984 | McGaughey et al. | 604/168 |
| 4,828,548 | 5/1989 | Walter | 604/168 |
| 4,904,240 | 2/1990 | Hoover | 604/168 X |

FOREIGN PATENT DOCUMENTS

| | | | |
|---|---|---|---|
| 2438245 | 9/1975 | Fed. Rep. of Germany | 604/900 |
| 9011098 | 10/1990 | PCT Int'l Appl. | 604/167 |

*Primary Examiner*—Randall L. Green
*Assistant Examiner*—Mary Beth Jones
*Attorney, Agent, or Firm*—Mark D. Miller

[57] ABSTRACT

A blood vessel entry indicator device is provided which includes a colored flexible membrane disposed within the transparent body of a hypodermic needle that is stretched over the proximal end of the needle cannula. As the needle reaches the inside of the blood vessel, pressure within the vessel is transferred through the cannula to the membrane which moves or inflates indicating that entry has been achieved. A stopper is provided for arterial use. Because it is pressure sensitive, the invention provides a positive indication of blood vessel entry, avoiding double puncture of the same blood vessel.

8 Claims, 1 Drawing Sheet

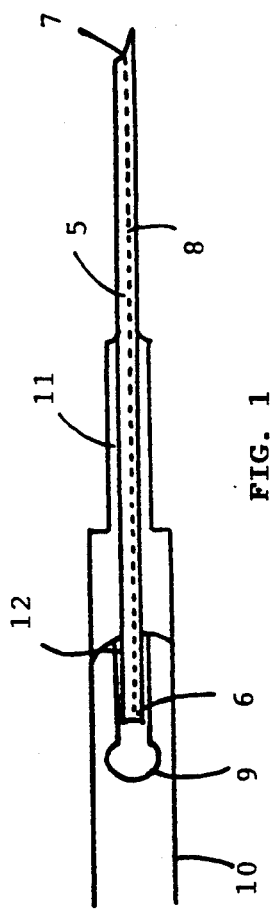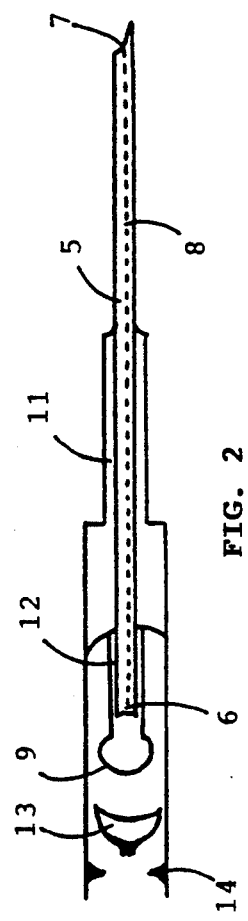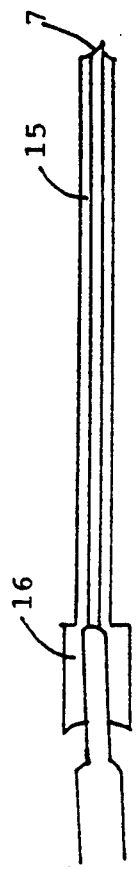

ENTRY INDICATOR DEVICE FOR ARTERIAL OR INTRAVENOUS NEEDLE

This is a continuation-in-part of copending application(s) Ser. No. 07/832,956 filed on Feb. 10, 1992, now abandoned.

BACKGROUND OF THE INVENTION

The present invention relates to a device for detecting when an intravenous or arterial cannula enters a vein or artery, and more particularly to a visually observable membrane which inflates or moves when the cannula comes into contact with the pressure of blood within a vein or artery.

Present intravenous and arterial cannulas depend upon a visual observance of blood itself in the hub of the cannula after the blood has flowed through the length of the cannula in order to indicate that the cannula needle has entered the vessel. Often, a cannula may puncture a blood vessel through both walls. When this happens using present cannulas, any back flow of blood may not be observed and the double puncture is undetected. This may result in improper administration of medication, hemorrhaging, collapse of the vein or artery, or other similar complications.

One method of addressing this situation is disclosed in U.S Pat. No. 5,030,207 to Mersch, et al. The Mersch device provides a fiber optic mounted around the cannula of the needle that is conformed to the distal end of the needle, so that as the distal end comes into contact with the blood at the interior of the vein or artery, that color is transmitted along the fiber optic to a magnifying system. However, the Mersch invention is complicated to manufacture, requires a certain amount of light to work properly, and may still allow the needle to puncture both walls of the vein or artery without being readily detected. The present is more reliable because it is activated by the pressure of the blood within the vessel.

SUMMARY OF THE INVENTION

The present invention overcomes the problems presented by existing vessel entry detection methods by providing a positive indication that a needle has entered a blood or other vessel through a response to the pressure inside the vessel. The indicator of the present invention will only be activate cannula needle is inside the vessel, so that the user can tell whether the needle exits the vessel or remains inside it. It will therefore make vessel insertion easier and more reliable while reducing the number of ruptured vessels.

It is therefore a primary object of the present invention to provide a device which positively indicates that a hypodermic needle cannula has entered a blood vessel.

It is a further important object of the present invention to provide a pressure sensitive device that positively indicates that a hypodermic needle cannula is in contact with the pressure of the fluid on the inside of a vessel.

It is a further important object of the present invention to provide a device that can readily indicate whether a hypodermic needle cannula has punctured through both walls of a vessel.

It is a further object of the present invention to provide a device for detecting the entry of a hypodermic needle cannula into a blood vessel so that a catheter may thereafter be inserted therein.

It is a further object of the present invention to provide a pressure sensitive device which indicates when a cannula of a hypodermic needle has come into contact with the pressure of blood flowing through a vein.

It is a further object of the present invention to provide a pressure sensitive device which indicates when a cannula of a hypodermic needle has come into contact with the pulsating pressure of blood flowing through an artery.

BRIEF DESCRIPTION OF THE DRAWINGS

FIG. 1 is a partially cut away longitudinal view of one embodiment of the invention for intravenous use.

FIG. 2 is a partially cut away longitudinal view of another embodiment of the invention for arterial use.

FIG. 3 is an environmental cross-sectional cutaway view of the invention showing it in contact with a vein (or artery) in combination with a catheter.

DETAILED DESCRIPTION OF THE DRAWINGS

Referring to the drawings wherein like reference characters designate like or corresponding parts throughout the several views, and referring particularly to FIG. 1, it is seen that the invention includes a transparent proximal body portion 10 including a hub assembly 11 for holding a needle cannula 5. The cannula 5 has a proximal end 6, a distal end 7, and a bore 8 therethrough.

In the intravenous embodiment shown in FIG. 1, membrane 12 is attached to the inside of hub 11 and covers over the proximal end 6 of the cannula 5. Membrane 12 includes a flexible portion 9 which may move or inflate in response to the pressure of blood or other fluid passing through bore 8 of cannula 5.

In the arterial embodiment shown in FIG. 2, in addition to membrane 12 and flexible portion 9, a separate terminator 13 is provided in order to stop the increased flex of portion 9 caused by the greater pressure from the inside of an artery as opposed to that of a vein.

FIG. 3 shows the present invention in use in connection with a catheter 15. Once there is motion in flexible portion 9 of either embodiment of the invention, the user knows that the pressure on the inside of the blood vessel been reached. Thereafter, catheter 15 may be inserted into the vessel by sliding catheter 15 and hub 16 along the outside of cannula 5.

DESCRIPTION OF THE PREFERRED EMBODIMENTS

In the preferred embodiment shown in FIG. 1 the hypodermic needle body 10 may be made of any suitable transparent or translucent material. Flexible membrane 12 and indicator portion 9 thereof should be made of a single piece airtight and watertight material (shaped like a mushroom) that is firmly attached to the inside of hub 11. Portion 9 should be colored so that movement thereof can be readily ascertained by visual observation through body 10.

The alternative embodiment of FIG. 2 simply adds the terminator 13 to prevent inadvertent spillage of blood or other fluid from higher pressure arteries or the like. The pointed terminator 13 should be shaped so that it allows portion 9 a small amount of room in order to flex, giving the entry detection signal to the user. Body portion 10 may have a restrictive collar 14 behind it, or the shape or length of terminator 13 may be modified in order to provide the necessary friction to stop membrane 9 from being over stretched.

It is to be understood that variations and modifications of the present invention may be made without departing from the scope thereof. It is also to be understood that the present invention is not to be limited by the specific embodiments

I claim:

1. A blood vessel entry indication device comprising a hypodermic needle assembly including a transparent body and a cannula, said cannula having a proximal and a distal end adapted for entry into a body and a flexible airtight membrane directly and sealingly engaging said proximal end wherein said membrane flexes in response to pressure changes in a blood vessel.

2. The invention described in claim 1 above wherein said membrane is colored in order to provide maximum contrast to said transparent body so that any movement thereof may be easily visually observed.

3. The invention described in claim 1 above wherein a terminator is mounted in said transparent body on the opposite side of said membrane from said cannula and adjacent to said membrane.

4. The invention described in claim 1 above wherein said cannula is used as an introducer for a catheter.

5. An entry indicator device for intravenous needle comprising:
   a. a hypodermic needle having a cylindrical transparent barrel body;
   b. a needle hub attached to the distal end of said body;
   c. a needle cannula attached to said hub, said cannula having distal end adapted for entry into a body and a proximal end; and
   d. a flexible membrane sealingly stretched over the proximal end of said cannula inside said body and attached to the inside of said needle hub wherein said membrane flexes in response to pressure changes in a blood vessel.

6. The invention described in claim 5 above wherein said membrane is colored in order to provide maximum contrast to said transparent body so that any movement thereof may be easily visually observed.

7. The invention described in claim 5 above wherein said cannula is used as an introducer for a catheter.

8. The invention described in claim 5 above wherein a terminator is mounted in said transparent body on the opposite side of said membrane from said cannula and adjacent to said membrane.

* * * * *